(12) United States Patent  
Toporek

(10) Patent No.: US 8,881,954 B2  
(45) Date of Patent: Nov. 11, 2014

(54) ACTUATOR FOR DISPENSING FLUID FROM A CARTRIDGE

(75) Inventor: Maurice Toporek, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/818,838

(22) PCT Filed: Aug. 24, 2011

(86) PCT No.: PCT/EP2011/064509  
§ 371 (c)(1),  
(2), (4) Date: Feb. 25, 2013

(87) PCT Pub. No.: WO2012/028498  
PCT Pub. Date: Mar. 8, 2012

(65) Prior Publication Data  
US 2013/0153606 A1    Jun. 20, 2013

(30) Foreign Application Priority Data

Aug. 30, 2010    (EP) ...................................... 10174457

(51) Int. Cl.  
*B65D 83/00* (2006.01)  
*A61M 5/145* (2006.01)

(52) U.S. Cl.  
CPC .... *B65D 83/0005* (2013.01); *A61M 2205/0266* (2013.01); *A61M 5/1452* (2013.01)  
USPC ....... 222/386; 222/326; 222/153.13; 222/384

(58) Field of Classification Search  
USPC ............ 222/386, 384; 60/527, 528; 417/44.1; 310/306, 307; 318/117  
See application file for complete search history.

(56) References Cited

U.S. PATENT DOCUMENTS

| | | | |
|---|---|---|---|
| 7,655,001 B2 * | 2/2010 | Petrakis ..................... | 604/890.1 |
| 2003/0229310 A1 | 12/2003 | Flaherty et al. | |
| 2005/0238503 A1 * | 10/2005 | Rush et al. ..................... | 417/322 |
| 2008/0132842 A1 * | 6/2008 | Flaherty ........................ | 604/151 |

FOREIGN PATENT DOCUMENTS

| WO | 03/103763 | 12/2003 |
|---|---|---|
| WO | 2006/113521 | 10/2006 |
| WO | 2009/118553 | 10/2009 |

OTHER PUBLICATIONS

International Search Report and Written Opinion for PCT/EP2011/064509, completed Nov. 11, 2011.  
International Search Report and Written Opinion for PCT/EP2011/064509, completed Feb. 3, 2012.  
International Preliminary Report on Patentability for PCT/EP2011/064509, mailed Mar. 14, 2013.

* cited by examiner

*Primary Examiner* — Paul R Durand  
*Assistant Examiner* — Donnell Long  
(74) *Attorney, Agent, or Firm* — McDonnell Boehnen Hulbert & Berghoff LLP

(57) ABSTRACT

The invention relates to an actuator for dispensing fluid from a cartridge, the actuator being configured to be moveable within the cartridge along the longitudinal axis of the cartridge and comprising a first radial element configured to face the dispensing opening of the cartridge, a second radial element configured to face in the opposite direction than the first radial element and a connecting element connecting the first and the second radial element and configured to extend along the longitudinal axis of the cartridge.

19 Claims, 10 Drawing Sheets

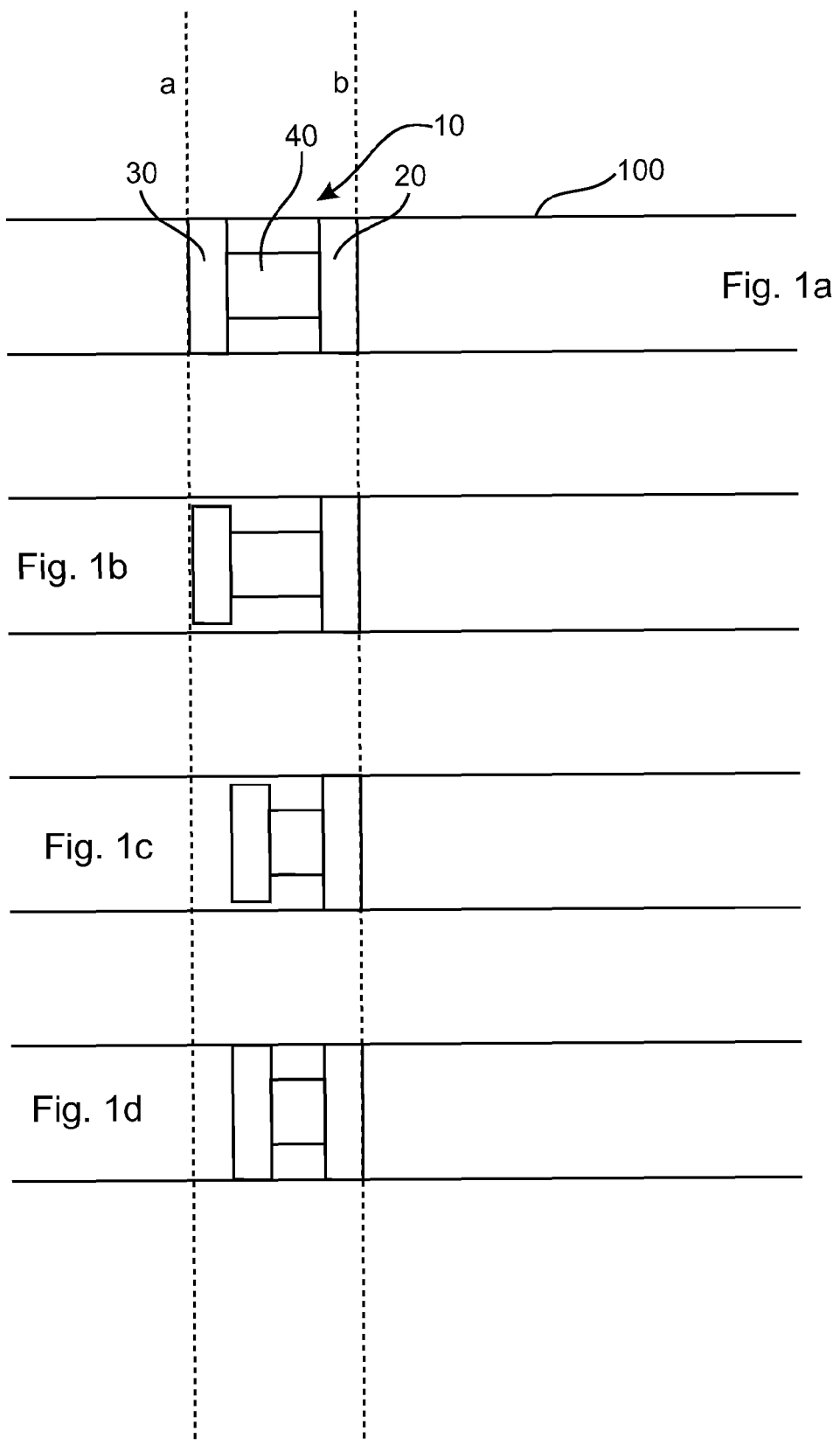

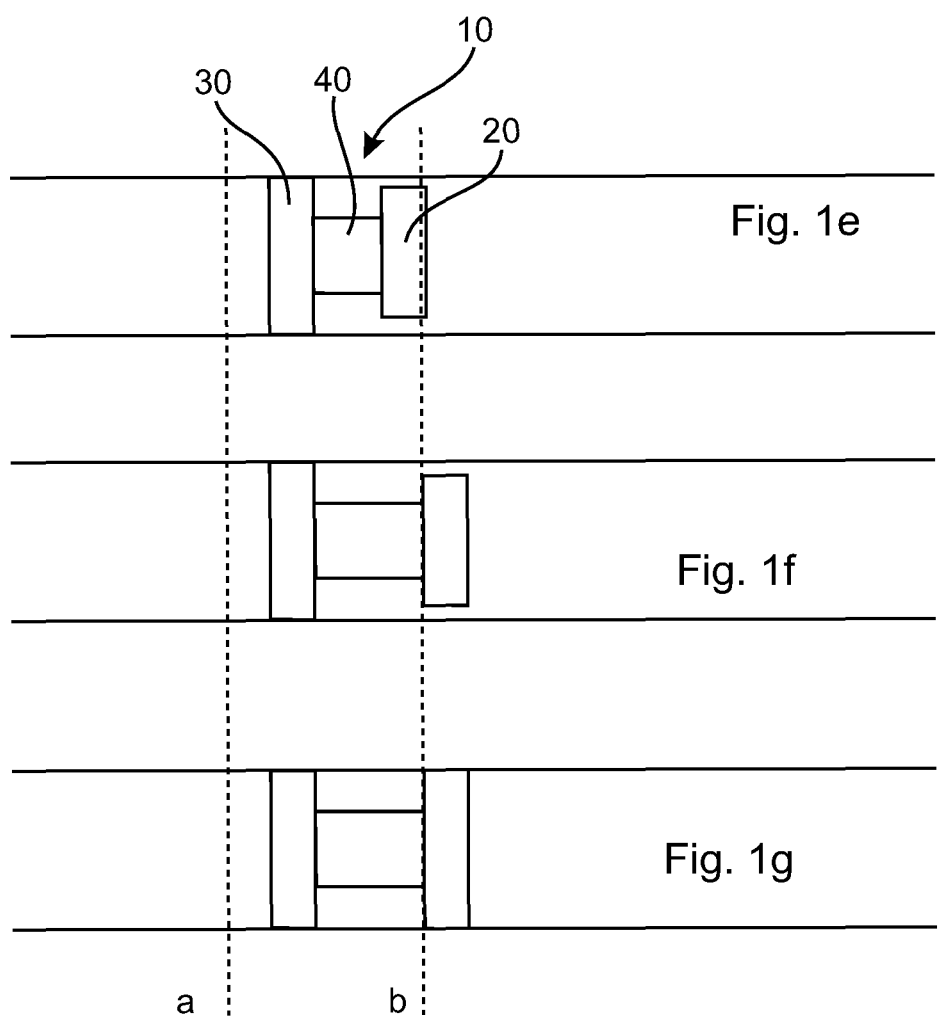

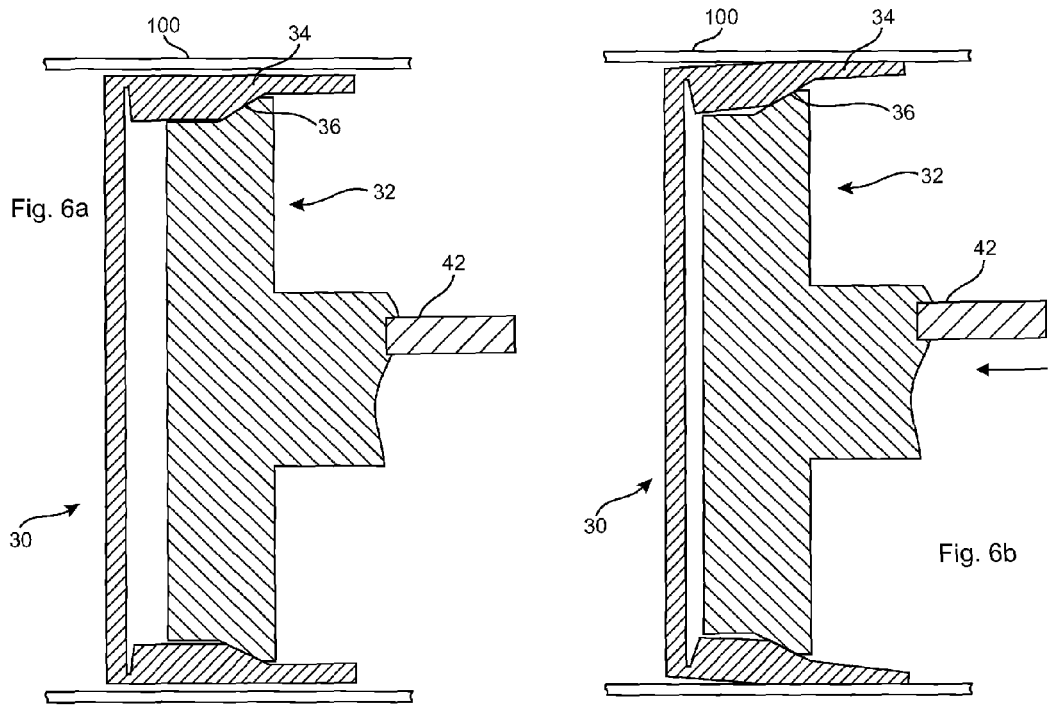

Fig. 7
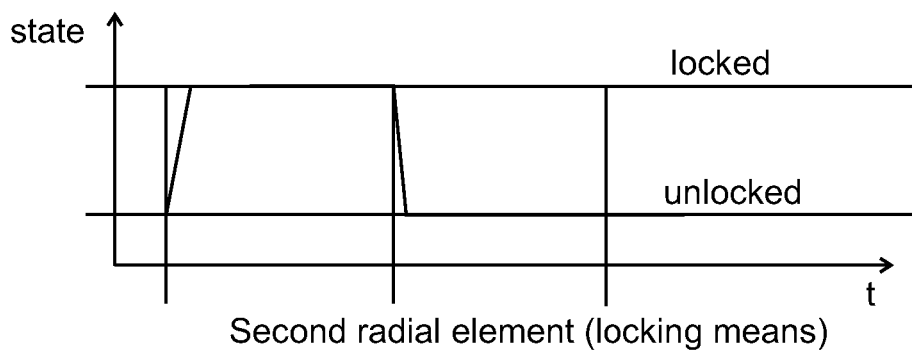
Second radial element (locking means)
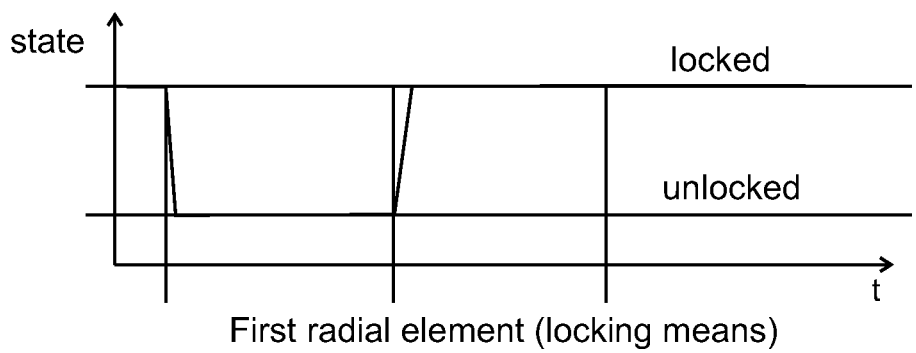
First radial element (locking means)
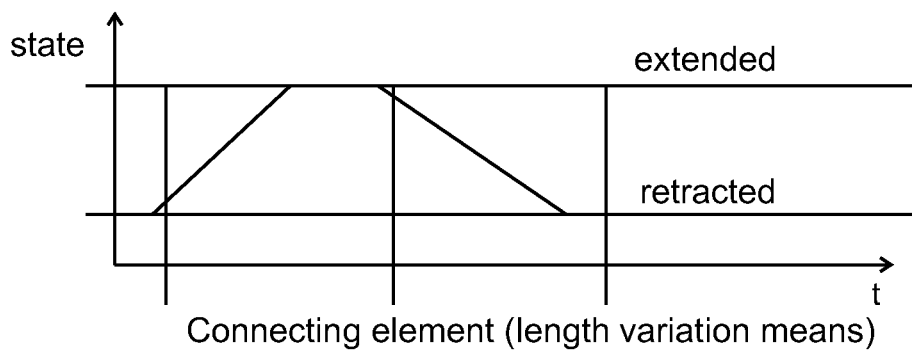
Connecting element (length variation means)

ACTUATOR FOR DISPENSING FLUID FROM A CARTRIDGE

CROSS REFERENCE TO RELATED APPLICATIONS

The present application is a U.S. National Phase Application pursuant to 35 U.S.C. §371 of International Application No. PCT/EP2011/064509 filed Aug. 24, 2011, which claims priority to European Patent Application No. 10174457.1 filed on Aug. 30, 2010. The entire disclosure contents of these applications are herewith incorporated by reference into the present application.

FIELD OF INVENTION

The invention relates to an actuator for dispensing fluid from a cartridge, the actuator being configured to be moveable within the cartridge along the longitudinal axis of the cartridge and comprising a first radial element configured to face the dispensing opening of the cartridge, a second radial element configured to face in the opposite direction than the first radial element and a connecting element connecting the first and the second radial element and configured to extend along the longitudinal axis of the cartridge. The cartridges are typically cylindrical in shape and have an outer wall or side wall made from glass.

BACKGROUND

Such actuators are known for dispensing fluids from cartridges. Such known actuators make use of caterpillar movement, but to achieve this, they are constructed to comprise typically three separate active elements. Two elements are necessary for blocking and releasing parts of the actuator and a third element is necessary to move the actuator along its longitudinal direction. Problem of such constructions is the complex structure of an actuator with three different and separate active elements as well as the high costs of such an actuator. First attempts to construct the two elements for blocking and releasing in a passive way led to the disadvantage of bad caterpillar movement. In particular such bad caterpillar movement with respect to the actuation way during one caterpillar cycle is of high disadvantage for the use in medical systems because it could lead to false dosage, in particular underdosage. For example in the use for insulin dispending, such an underdosage could be even life-threatening.

SUMMARY

The aim of the present invention is to solve the problems, of known actuators described above.

Aforesaid aim is achieved by an actuator according to independent claim 1 as well as the use of an actuator according to independent claims 17 and 18 and by a system according to independent claim 15.

An inventive actuator for dispensing fluid from a cartridge is configured to be moveable within the cartridge along the longitudinal axis of the cartridge and comprises:
- a first radial element configured to face the dispensing opening of the cartridge,
- a second radial element configured to face in the opposite direction than the first radial element and
- a connecting element connecting the first and the second radial element and configured to extend along the longitudinal axis of the cartridge, Further the connecting element comprises length variation means for variation of the longitudinal length of the connecting element and the first and the second radial element each comprise locking means for releasably locking each of the first and the second radial element separately against movement along the longitudinal axis of the cartridge. The locking means are configured to be activated and released by the length variation means depending on the variation of the longitudinal length of the connecting element. The locking means are passive locking means without active drive, triggered by the direction of the length variation movement of the length variation means. Further, the locking means comprise stopping parts which are moveable in the radial direction of the actuator.

By the use of such an inventive actuator, a caterpillar movement of the actuator within a cartridge can be carried out. Such caterpillar movement results from configuration of the locking means in dependency from the length variation means as well as the length variation itself. The caterpillar movement is described as follows:

The inventive actuator, which is placed within a tube like container, e.g. a cartridge, or which can already be contained within such a cartridge, is located such that the longitudinal axis of the actuator and the longitudinal axis of the cartridge extend coaxial. The start position can be either with the length variation means in contracted or extended position. In the extended position of the length variation means, the actuator has an extended longitudinal length and in the contracted position of the length variation means, the actuator has a reduced longitudinal length. Both situations are possible for starting the caterpillar movement of the actuator. As an example, the starting position is with the actuator having an extended length and the length variation means in extended position. In a first step, the length variation means is moved from the extended position to the contracted position, thereby causing the locking means of the second radial element to unlock and causing the locking means of the first radial element to lock. Continuing the movement to the contracted position of the length variation means, the second radial element, which is connected with the connecting element, is pulled by such connecting element, in particular by the contraction of the length variation means, in the direction of the dispensing opening of the cartridge. At the end of the contracting movement of the length variation means, the second radial element has still a locking means in unlocked position, the first radial element has still a locking means in locked position and the actuator itself is in contracted situation having a reduced length.

Following afore said situation, the length variation means start to carry out a movement to extend from the contracted position to the extended position. Due to the started movement, the locking means of the second radial element change their status from unlocked to locked and the locking means of the first radial element change their status from locked to unlocked. In other words, the extension movement of the length variation means pushes the first radial element in the direction of the dispensing opening of the cartridge and the actuator's longitudinal length increases. This second part of the actuator movement is responsible for reducing the remaining volume of the cartridge between the first radial element of the actuator and the dispensing opening of the cartridge and thus is responsible for dispensing fluid out of the cartridge.

As described in detail above, the inventive actuator can carry out the complex caterpillar movement by only two different movements of the length variation means, namely the contraction and the extension movement. The locking means of the two radial elements follow the length variation means automatically to perform the caterpillar movement of the actuator.

The locking means can be formed by one single part or also by multiple parts of the respective radial element. In particular it is possible that different parts of the locking means can be moved relative to each other. Also subparts of the radial element can provide integrally formed locking means or at least parts of it. For example the locking means can comprise sliding ramps, rotating discs or radially extending pins.

According to one embodiment of the present invention, the actuator is characterised in that the locking means are passive locking means without active drive. According to such an embodiment of the present invention, the actuator can be constructed in a cheap and simple way. No cost-intensive and complex additional drives are necessary for the activation and the release of the locking means. The passive construction of the locking means also has the advantage that no false movement of the actuator is possible. The passive construction can for example be a direct or indirect mechanical connection between the length variation means and the locking means. Following such a mechanical solution for the passive locking means, the locking and unlocking action is coupled directly to the length variation means. For example, an extension or increase of the longitudinal length of the connecting element results in the locking of the second radial element and the unlocking of the first radial element. The reduction of the length of the connecting element results the other way round in the unlocking of the second radial element and locking of the first radial element. Thus, by constructing the locking means in a passive way, the caterpillar movement of the inventive actuator is also carried out automatically, following the length variation of the variation means.

It should be noted that the locking means is in a locked status, when the locking means is prevented from movement along the longitudinal axis of the container or cartridge.

According to an embodiment of the present invention, the actuator is characterized in that the locking means are configured to releasably engage with the outer wall of the cartridge. The engagement will lock the actuator and prevent the actuator from movement along the longitudinal axis of the container or cartridge. In particular, the engagement can lock the locking means and prevent the locking means from movement along the longitudinal axis of the container or cartridge.

Furthermore an inventive actuator can have locking means which comprise stopping parts which are moveable in the radial direction of the actuator. The stopping parts are one possibility to lock the respective radial element against movement along the longitudinal axis of the cartridge. The stopping parts can for example be constructed as parts of an outer housing of the respective radial element which is made of resilient material. Acting on such stopping parts in radial direction can push the stopping parts against the outer wall of the cartridge and therefore prevent movement along the longitudinal axis of the cartridge by friction between the outer wall of the cartridge and the stopper parts. Due to resilient material of the stopping parts, they return to the unlocked position as the Acting in radial direction is reversed.

The locking means is activated or in a locked position when the stopping parts are moved radially outward. The locking means is released or in an unlocked position when the stopping parts are moved radially inward.

Also an inventive actuator can be characterised in that the locking means of both radial elements comprise a mechanical connection of corresponding ramps. Using ramps can be of an advantage in particular when each locking means comprises at least two parts being moveable against each other in longitudinal direction of the actuator. Both of the parts comprise ramps with more or less the same gradient. Movement of the two parts against each other will result in the two ramps of moving against each other and therefore will result in a radial movement of at least one of the two parts. If the first part is in the centre of the actuator and therefore fixed as to its radial extension, the second part moved radial outward or inward, depending on the direction of the gradient of the ramps and depending on the direction of the movement of the two parts. The second part can for example be directly a stopping part as described above. But also a second part acting on separate stopping parts is possible within the scope of the present invention. To carry out the caterpillar movement, the corresponding ramps of the two radial elements are advantageously located with the same direction of the gradient for the first and the second radial element. Which is to say, that corresponding ramps of both radial elements have the same direction of gradient. On the other hand, the mechanical connection of this example is a releasable sliding connection of the ramps of each radial element.

According to the present invention the first radial element of an inventive actuator further comprises interface means for transferring the movement of the actuator to the fluid contained within the cartridge. The interface means can for example comprise a sealing part which is able to seal the volume of the cartridge in the direction of the dispensing opening of the cartridge against the rest of the actuator. The sealing part can for example be of similar shape as the profile of the cartridge with a little more extension in radial direction and made of resilient material. Such a sealing member can ensure the dispensing of all fluid contained within the cartridge. Moreover, such sealing part prevents the fluid from entering the actuator and for causing damage within the actuator.

The interface means of an inventive actuator can for example be releasably connected to the first radial element of the actuator. Such an inventive configuration has the advantage that the interface means can be released from the actuator after the usage in a cartridge and for example can be replaced by a new interface means. Such a replacement can offer the possibility of multiple use of the actuator within different cartridges for example with different profiles or containing different fluids. An inventive actuator for multiple usage further reduces the cost of such usage.

Moreover, the interface means can for example comprise a circumferential seal for sealing the fluid against leaking between the first radial element and the cartridge. In particular for using electrical or partly electrical length variation means, the leakage of fluid form the cartridge to the actuator could cause problems or in a worst case, break down of the actuator. The other way round, in particular with respect to sensible fluids like medicaments being dispensed into a human body, contamination of the fluid from outside can be prevented by the use of a circumferential seal.

An inventive actuator can be characterised in that the interface means comprise a geometry for transferring the movement of the actuator to passive closing means of the cartridge. According to this embodiment, the actuator is active and separate from the cartridge as well as from the passive closing means. Such passive closing means can for example be some kind of moveable plunger or moveable piston, which also comprises a sealing element for closing the cartridge at one end and for acting as a dispensing plunger or piston on the fluid contained within the cartridge. The advantage of such a configuration is the fact that standard cartridges with standard closing means can be used. A standard passive closing means, normally the piston or plunger driven by a piston rod, acts to dispense the fluid out of the cartridge. According to an inventive configuration, instead of the piston rod, the actuator is used for acting on the passive closing means and therefore to dispense the fluid out of the cartridge.

Moreover, the inventive actuator can comprise a length variation means with at least one element that varies the length upon stimulation of either physical, chemical, or biological nature or a combination thereof. As physical phenomenon's for example, the piezo effect, magnetism or shape memory effects can be used. Chemical stimulation can be carried out for example by using differences in the aggregate state, for example between crystallized and liquid state. An example for biological stimulation is the use of active liquids, which change their state according to the appliance of current.

An inventive actuator can be varied with respect to the place of the stimulation of the length variation means. It can be distinguished between internal and external stimulation. "Internal stimulation" is to be understood as a stimulation which is generated within the actuator. Such an actuator is very independent from external sources and thus can be used very flexible. In particular active means for stimulation such as electrical sources, heat sources or the like are integrated within the actuator. Internal stimulation can be characterized by the fact that the stimulating means is part of the actuator as in case of a shape memory material that is, for example, stimulated by an electrical current for heating inside the actuator. On the other hand "external stimulation" is to be understood as a stimulation of the length variation means from outside of the actuator. Beside reduction of flexibility, such a solution takes the advantage that active means like batteries or heat sources can be used which are already located within a device using the actuator. That way the actuator becomes smaller, less complex and thus less expensive. External stimulation can be characterized by the fact that the stimulating means is not part of the actuator as in case of an actuator that is stimulated by a magnetic field induced by a solenoid around the container.

According to a further embodiment of the present invention, the actuator is characterised in that the length variation means comprises a shape memory material. Such shape memory material can for example be a shape memory alloy like nickel or titanium alloy. The shape of such a material in particular depends on its temperature. That way, heating and/or cooling elements can be used for the variation of the length of the actuator. For example, if a material is used which extends significantly under heat, a heater can be used for the extension movement of the length variation means. If the heater is shut off, the material will cool down and therefore will contract again. Such two movements can be cycled such that the inventive caterpillar movement can be carried out.

The length variation means of an inventive actuator can for example comprise a piezoelectric part. The use of a piezoelectric part for the length variation means has the advantage that a very fast reaction can be achieved. The time gap between the activation of the length variation means, its reaction and therefore the dispensing of the fluid is reduced.

The length variation means of an inventive actuator can for example comprise magnetic elements. The use of magnetic elements for the length variation means has the advantage that a very fast reaction can be achieved. This fast reaction applies to both the contraction and extension motion. In addition this activation includes active extension. In effect, using magnetic elements results in a short cycle time for a cycle of contraction and extension movement. Such a magnetic part could for example be a static magnet or a dynamic magnet such as a coil magnet or solenoid or any combination thereof. In one example an electrical current through the solenoid induces a magnetic field which forces the static magnet to move, resulting in a contractive movement of the length variation means. An electrical current in opposite direction would bring the length variation means to its extended start shape. Having disclosed this configuration it is clear to anyone skilled in the art to vary the configuration by altering any one of position and number of static and dynamic magnet or combination thereof. This includes in particular one example configuration where two static magnets define a shape of the length variation means and this shape is changed in response to a magnetic field external to the length variation means. For example a solenoid can be configured around a container, where an inventive actuator is positioned inside the container, thus stimulating the length variation means inside the inventive actuator inside the container.

Furthermore, an inventive actuator can further comprise pull back means for pulling back the actuator away from the dispensing opening of the cartridge. Using a pull back means for an inventive actuator has the advantage that the actuator can be pulled back very fast without the use of a caterpillar movement. Moreover, due to the simple and cost efficient inventive construction, the caterpillar movement of the actuator is only able in one direction in preferred embodiments. In particular at those embodiments, the pull back means enable the multiple usage of the inventive actuator. Such pull back means can for example be a wire for actively pulling back the actuator. However, the pullback means can for example also take advantage of magnetic effects.

The length variation means can also be configured to carry out at least the extension movement fast. The use of inventive actuators for dispensing medical fluids is particular crucial as to the reaction time between the request of dispensing and the actual time of dispensing. Such time gap can be reduced for example by speeding up the extension movement of the length variation means. Due to the fact that the extension movement of the length variation means is related to the dispensing of the fluid, the contraction movement of the length variation means can be carried out slow in relation to the extension or extension movement. The contraction movement only prepares the actuator for the next dispensing step, namely the following extension movement or in other words, the upcoming caterpillar cycle. By using such characteristics, length variation means according to the present invention need only be as fast as required for the extension or contraction movement. Therefore also cheaper constructions of the length variation means of the present invention are possible. However, with an inventive actuator, also very fast injections, so called bolus injections can be possible.

One further aspect of the present invention is the use of an inventive actuator for dispensing medical fluids.

It is also an aspect of the present invention to provide a system comprising at least one cartridge, at least one inventive actuator and at least one control means for controlling the length variation means of the actuator.

A further aspect of the present invention is the method of utilization of an inventive actuator.

In an advantageous embodiment of the present invention, the maximum length variation of the length variation means may be smaller than the length variation necessary for one delivery step of delivering liquid from the container. In other words, each delivery step may be carried out by more than one, for example at least two actuation steps of the actuator. That way, the resolution of possible delivery steps may be defined by the maximum length variation of the length variation means. Such an embodiment can be constructed in a simple and easy way due to the fact that the actuator only needs to carry out full steps. The delivery step therefore may consist of multiple actuator steps. Executing a delivery step delivers a certain amount of liquid from the container, e.g. an amount or dose that has been selected prior to dispense.

On the other hand, in particular in situations when specific accuracy as to the amount of delivery is needed, a more complex actuator can be of advantage. In such an embodiment of the present invention, the maximum length variation of the length variation means may be greater than the length variation necessary for one delivery step of delivering liquid from the container. In other words, one deliver step may be carried out by only a part of an actuator step. For example, the actuator can carry out 40% of its maximum length movement and stop the delivery of liquid. Following, the actuator is moved in a start position in which the full 100% of length movement is available for the following delivery step. Such an embodiment may be of advantage in situations when a lot of different volumes shall be delivered by one and the same actuator with high accuracy. It is more complex as to its construction, but more flexible as to its use.

An inventive method can be carried out such that specific doses of the liquid medicament may be delivered out of a container by the actuator. That means that for example the specific doses could be predefined within the system or within the actuator, or that medical staff could configure the specific dose to be delivered. In particular it could be advantageous, in case the dose to be delivered would be relatively small, for example between 1 µl (micro liter) and 10 µl (micro liter). In general, doses between 10 µl (micro liter) and 100 µl (micro liter) might be advantageous.

For further advantages, a system could be provided that uses an inventive actuator together with a conventional mechanism, for example a piston rod activated mechanism, e.g., in a system for dispensing fluids. That way, for example, the conventional piston rod activated mechanism could be used to deliver relatively large amounts of liquid from a first container, wherein the inventive actuator would be used to deliver specific, relatively small amounts of a further liquid from a second container. That way, the actuator could use the same common system components like battery, control unit, display, interfaces, etc. that are already existing for the conventional mechanism. Thus a very compact and cost effective two-component medication delivery system is possible. For example the second component could be an additive, which is added to the main medicament, for example due to changing parameters. A small carry-on delivery-device can that way react very flexible on changes in outer parameters.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-S er-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5-des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Exemplary embodiments of the present invention have been described. Those skilled in the art will understand, however, that changes and modifications may be made to these embodiments without departing from the true scope and spirit of the present invention, which is defined by the claims.

The advantages of various aspects of the present invention will become apparent to those of ordinary skill in the art by reading the following detailed description, with appropriate reference to the accompanying drawings.

BRIEF DESCRIPTION OF THE FIGURES

The present invention is further described with respect to the embodiments, depicted in the figures. Such figures show:

FIGS. 1a-1g illustrate schematic views of the different steps of the caterpillar movement FIG. 6a illustrates a further embodiment of a second radial element with locking means in unlocked position FIG. 6b illustrates a second radial element of FIG. 6a with locking means in locked position FIG. 7 illustrates diagrams showing the relation of the locking means and the length variation means

DETAILED DESCRIPTION

Figure 2A:
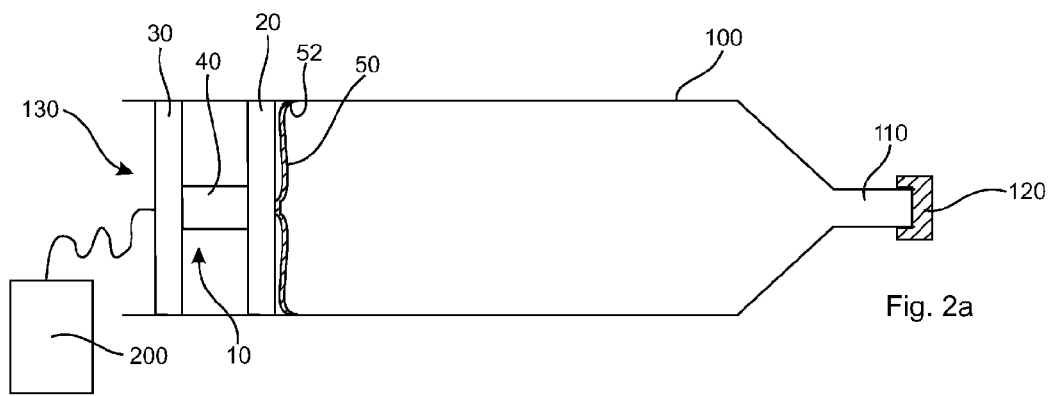
FIG. 2a illustrates a first embodiment of an inventive actuator

With respect to FIGS. 1a to 1g, the caterpillar movement of an inventive actuator 10 will be explained in the following. It has to be noted that FIGS. 1a to 1g only show a schematic illustration of an inventive actuator 10. The starting situation depicted in FIG. 1a is with a length variation means 42, located within the connecting element 40 and visible in FIGS. 5a, 5b, 6a, 6b, 8, 9, in its extended position. However, the starting situation could also be any other of the situations depicted in one of the FIGS. 1a to 1g, due to the fact that the caterpillar movement is the result of cycling the situations and movements of such Figures. To visualize the caterpillar functionality better, the ends of both radial elements 20 and 30 define the absolute starting positions labeled "a" and "b" in FIGS. 1a to 1g. At this point it has to be defined that the expression "locked position" has to be understood as locking the respective radial element 20 and 30 against movement in the longitudinal direction of the actuator 10.

In FIG. 1a, the length variation means 42 is in its extended position. Both locking means 22 and 32 (see FIGS. 5a, 5b and 6a, 6b respectively) of the first radial element 20 and the second radial element 30 are in its locking position. However, it has to be noted that in some embodiments of an inventive actuator 10, such a situation is not possible due to the fact that both locking means 22 and 32 can not be in their locking position at the same time. Therefore, this step can be spared out for such embodiments also covered by the present invention.

In FIG. 1b, the locking means 32 of the second radial element 30 has moved into its unlocked position. Such movement is triggered by the start of the length variation means 42 moving from the extended position in the direction of its contracted position. As it can be seen in FIG. 1b, the second radial element 30 has already moved a little bit away from its starting position a by being pulled as well as unlocked by the start of the contraction movement of the length variation means 42.

FIG. 1c shows the situation after the contraction movement of the length variation means 42 has been fully carried out. The length variation means 42 and therefore also the overall actuator 10 is in its fully contracted position, namely having its shortest length. Due to the fact that the length variation means has not carried out any change in its movement direction, namely it has only carried out the contraction movement, the locking means 32 of the second radial element 30 is still in its unlocked position, wherein the locking means 22 of the first radial element 20 still remains in its locking position.

In FIG. 1d, the length variation means 42 has already started its extension movement. As it can be seen in this figure, due to the relation between the length variation means 42 and the locking means 22 and 32, the locking means 32 of the second radial element 30 has thereby changed its position into the locked position. The situation depicted in FIG. 1d may in some embodiments be not possible as already explained with respect to FIG. 1a. However, in such embodiments, the caterpillar movement will just leave out the FIGS. 1a, 1d and 1g and the actuator will transit between the situations depicted in the respective adjacent figures.

FIG. 1e shows the situation after the extension movement of the length variation means 42 has already caused the locking means 22 of the first radial element 20 to change into its unlocked position. Therefore, the first radial element 20 has already started to move away from its staring position at the line labeled "b" and to start the dispensing action. Thereby, the length variation means 42 continue its extension movement pressing against the locked second radial element 30 and thus pushing the first radial element 20 to the right.

In FIG. 1f, the end of the extension movement of the length variation means 42 is depicted. The length variation means 42 and thereby also the connection element 40 as well as the overall actuator 10 have arrived in its fully extended position. The locking means 32 of the second radial element 30 still remain in its locked position.

FIG. 1g shows the situation with both locking means 32 and 22 in its locked position and thus is equal to the starting position depicted in FIG. 1a, but moved away from the labeled lines "a" and "b". Once more it has to be noted that the situations shown in FIGS. 1a, 1d and 1g are not essential for the caterpillar movement and can be spared out in some embodiments of an inventive actuator 10.

To make sure that in some situations the actuator 10 is ready to use, namely ready to dispense, the starting position can be used as depicted in FIG. 1c. In this position, the dispensing action by the extension of the length variation means 42 can be started immediately.

Figure 2B:
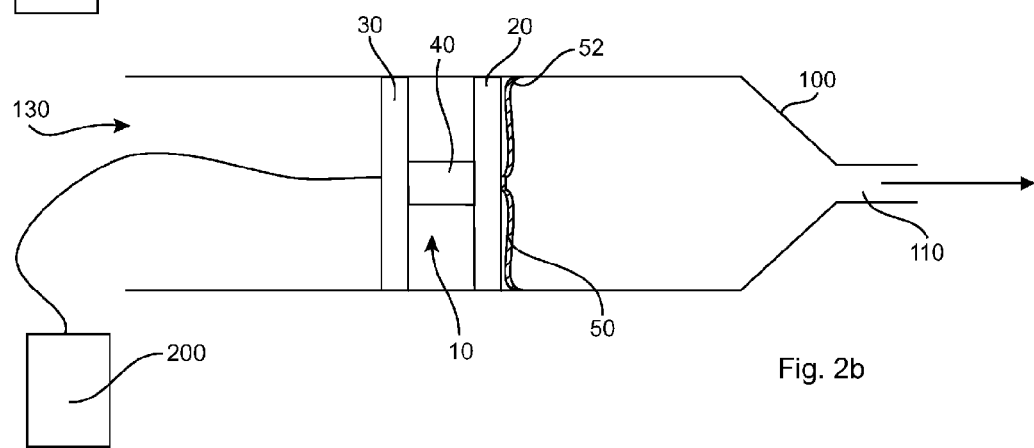
FIG. 2b illustrates an actuator of FIG. 2a during dispensing
Figure 3A:
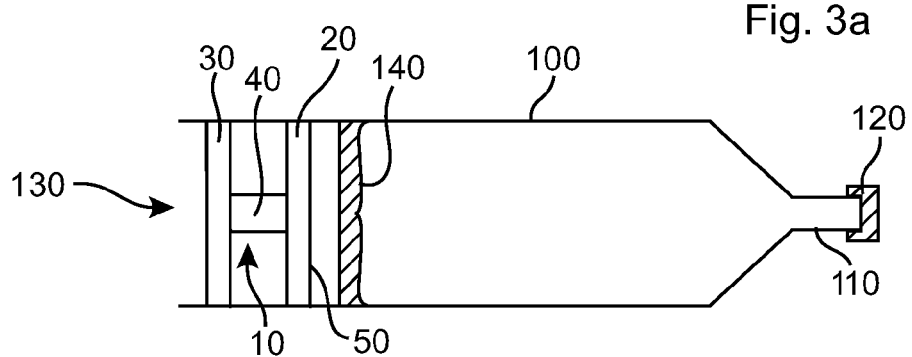
FIGS. 3a-3d illustrate further embodiments of an inventive actuator in different steps of usage
Figure 3B:
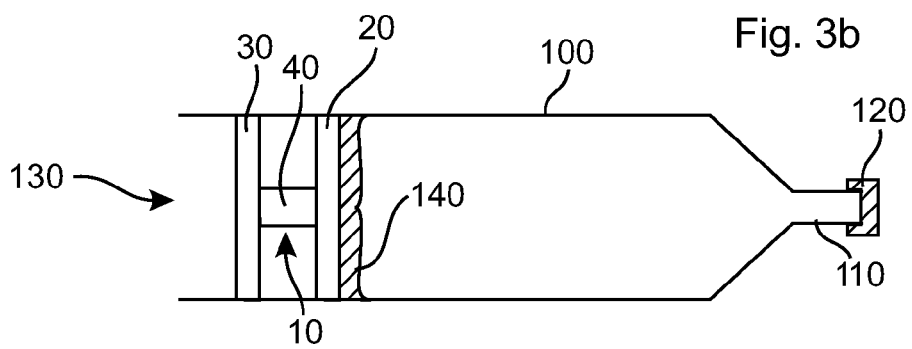
Figure 3C:
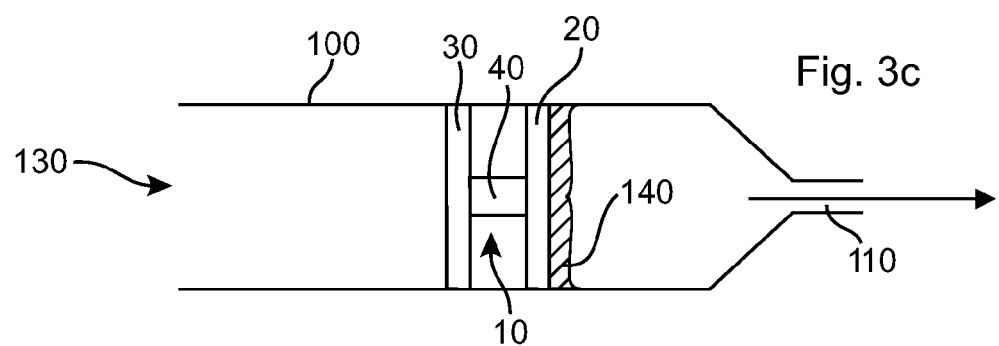
Figure 3D:
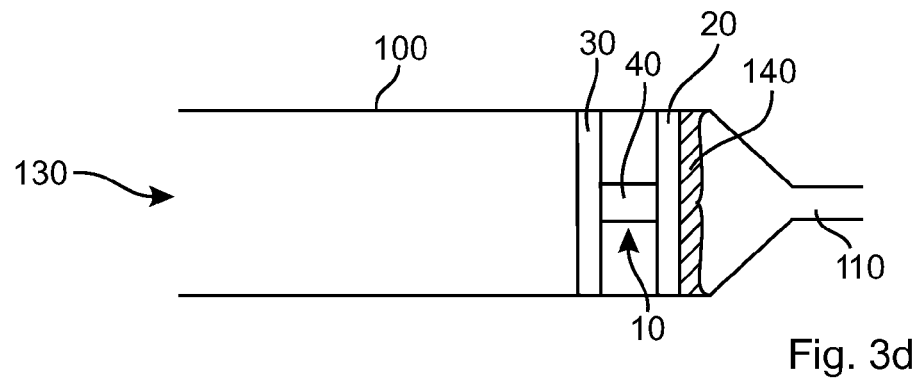

FIGS. 2a and 2b show a further embodiment of the inventive actuator 10. FIG. 2a shows such actuator 10 in its starting position at the filling opening 130 of a cartridge 100. The actuator 10 comprises a second radial element 30 facing the filling opening 130 of the cartridge 100 as well as a first radial element 20, facing the dispensing opening 110 of the cartridge 100. Both radial elements 20 and 30 are connected by a connecting element 40. Such connecting element includes a length variation means 42 not shown in this figure. The length variation means 42 of this embodiment comprises a shape memory material which length can be adapted by applying different temperatures. Therefore, the length variation means 42 further comprise a heater, which can apply a higher temperature to change the length of the length variation means 42.

The length variation means 42 of the connecting element 40 are controlled by control means 200 outside of the cartridge 100. That control means 200 can for example be a micro controller or a computer located in a dispensing system or any external housing. The control means 200 also comprise a control connection to the actuator 10 to transmit signals to the length variation means 42 resulting its length variation. Signals can also be transmitted in the contrary direction to get information about the present position or situation of the actuator to the control means 200. Beside the illustration of a hardware control connection from the control means 200 to the actuator 10, also other kinds of control connections can be used. In particular radio control connections like Bluetooth can be useful.

FIG. 2b shows the situation during dispensing. After several caterpillar movement of the actuator 10, such actuator 10 has arrived in the position of FIG. 2b. By carrying out such movement away from filling opening 130 of the cartridge 100 in the direction of the dispensing opening 110 of the cartridge, the volume defined by the actuator 10 and the outer wall of the cartridge 100 in the direction of the dispensing opening 110 is reduced. That reduction of volume causes fluid stored within that volume of the cartridge 100 to be dispensed through the dispensing opening 110.

Moreover, the actuator 10 of FIGS. 2a and 2b has an interface means 50 which is connected releasable to the first radial element 20. Such interface means 50 is configured to be the interface between the actuator 10 and the fluid contained within the cartridge 100. To achieve this, in the present embodiment, the interface means 50 comprise a circumferential seal 52 keeping a sealing force in the radial direction on the outer wall of the cartridge 100. This circumferential seal 52 prevents fluid to enter the volume of the cartridge 100 in which the actuator 10 is located. Beside the prevention of possible disturbance of the functionality of the actuator due to presence of liquid in such volume, the dispensing action is not handicapped by fluid which does not leave the cartridge through the dispensing opening 110.

FIGS. 3a to 3d show a further embodiment of the present invention. The actuator 10 of such embodiment is configured to act not directly on the liquid stored in a cartridge 100, but is configured to act against a passive closing means 140. Such passive closing means may be a plunger which is used to close the cartridge 100 after filling step in the production process. The passive closing means therefore are part of the one-way cartridge and also for one-use-only. The actuator 10 of this embodiment comprises interface means 50 at the first radial element 20 in shape of a generally flat surface which can transmit the force applied by the longitudinal movement of the actuator 10 on the passive closing means 140. Such passive closing means also comprise a circumferential seal which is sealing not only after the filling step of the production process and during transportation and storage of the cartridge 100, but also during the dispensing action by using the caterpillar movement of the actuator 10.

Figure 4A:
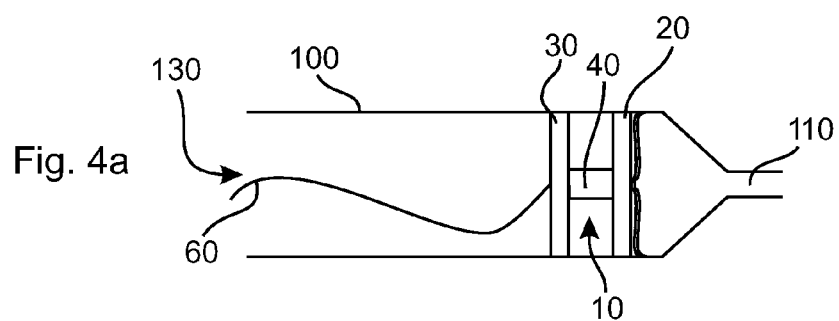
FIGS. 4a-4e illustrate further embodiments of an inventive actuator in different steps of usage
Figure 4B:
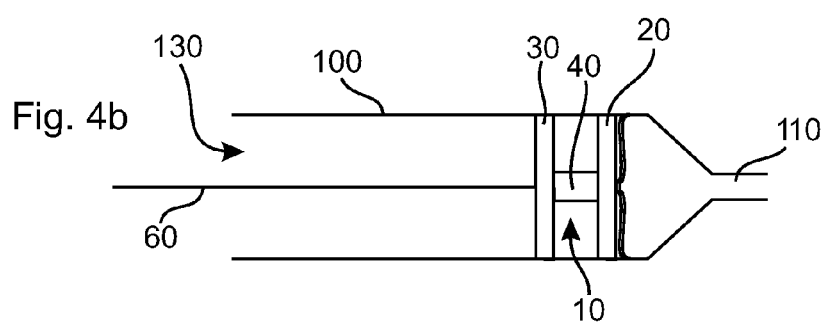
Figure 4C:
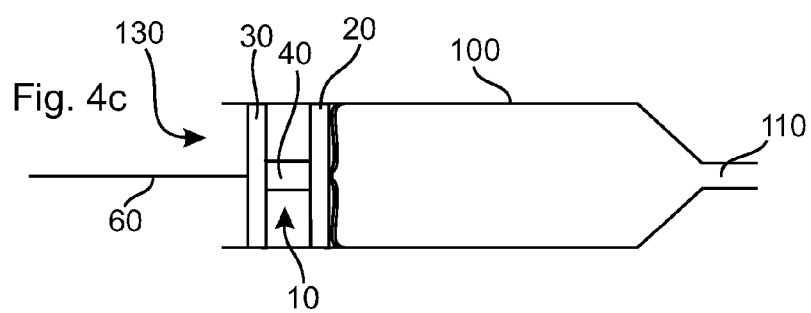
Figure 4D:
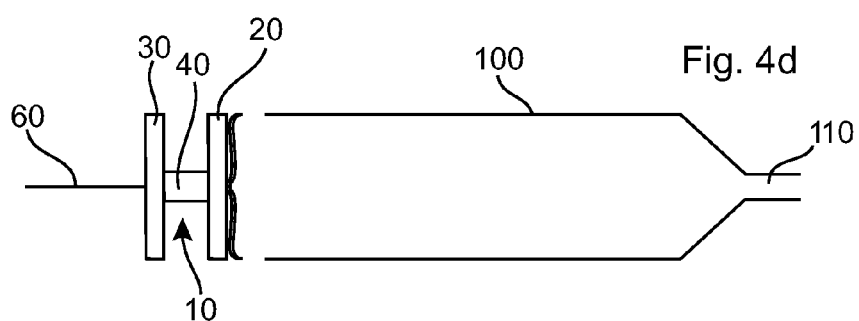
Figure 4E:
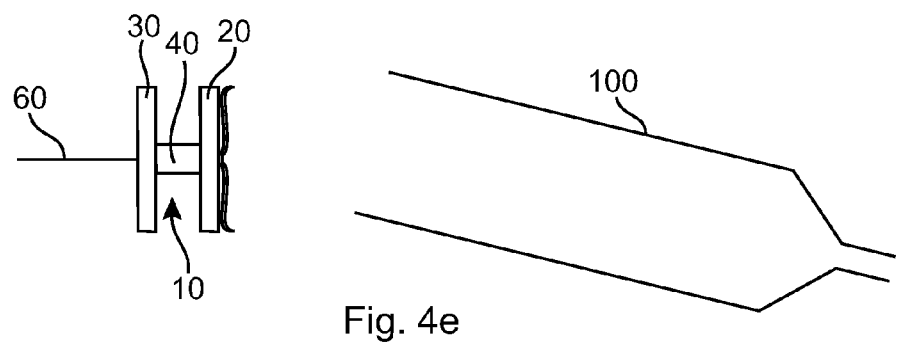

FIGS. 4a to 4e show a further embodiment of the inventive actuator 10. Such embodiment is similar to the embodiment depicted in FIGS. 2a and 2b, but further pull back means 60 are provided. The pull back means 60 of this embodiment are constructed as a pull back wire which is loose during the operation of the actuator 10, in particular during dispensing by using the caterpillar movement. FIG. 4a shows the end of all dispensing actions, for example after multiple doses have been dispensed over a period of time like hours, days or even weeks. To make sure that the actuator 10 can be used with further, filled cartridges 100, the actuator 10 has to be moved out of the cartridge 100. The actuator 10 of this embodiment has a mechanical relation between the length variation means 42 and the locking means 22 and 32 which allows caterpillar movement only in the direction from the filling opening 130 to the dispensing opening 110 of the cartridge 100. Therefore, a contrary movement of the actuator to retrieve it out of the cartridge 100 is impossible. To have the opportunity to use the actuator 10 again, the pull back means 60 is straightened as shown in FIG. 4b. In a next step the actuator 10 is pulled back from the dispensing opening 110 of the cartridge 100 in the direction of the filling opening 130 as shown in FIG. 4c. The actuator 10 is pulled further by using the pull back means 60 to leave the cartridge 100 through filling opening 130. That situation is depicted in FIG. 4d. In FIG. 4e shows the situation after the actuator 10 has left the cartridge 100 which can be disposed and replaced by a full cartridge 100.

Figure 5A:
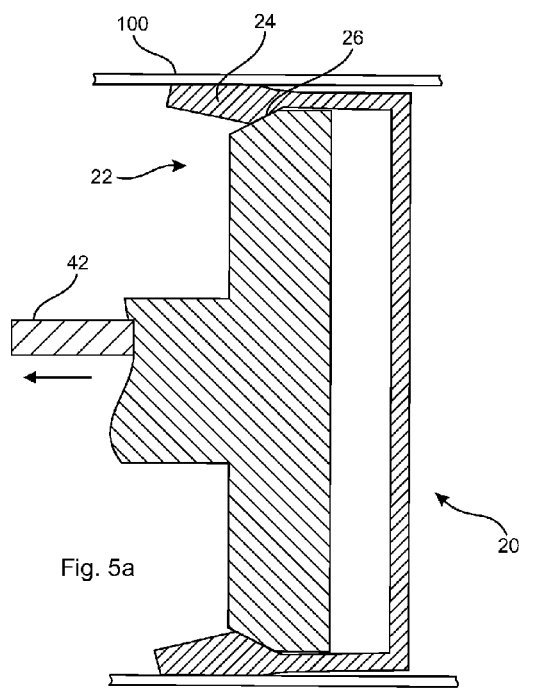
FIG. 5a illustrates a further embodiment of a first radial element with locking means in locked position
Figure 5B:
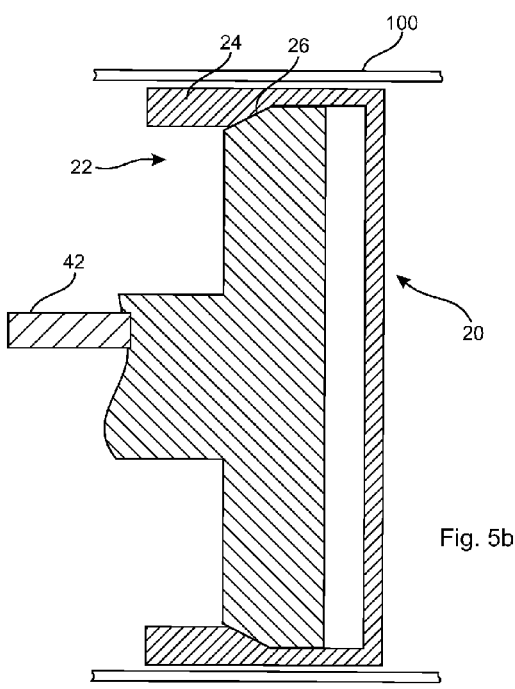
FIG. 5b illustrates a first radial element of FIG. 5a with locking means in unlocked position

FIGS. 5a and 5b depict one embodiment of a first radial element 20. Such first radial element 20 comprises an embodiment of a locking means 22 which is correlated with the movement of the length variation means 42 in the connecting element 40. The locking means 22 of this embodiment comprise in general two different parts. The first part of the locking means 22 is a sub-part of a general circle profile and is coaxial with the longitudinal axis of the actuator 10 as well as of the cartridge 100. Radially outside of the first part, a second part is provided by a sub-part of the radial element 20, formed like a housing. Such housing is formed like a hollow cylinder, closed at one axial end by a circular plate. The other axial end of the cylinder is open to receive the sub-part of the first part of the locking means 22. The first and the second part contact each other with corresponding ramps 26 of the first and the second part of the locking means 22. Therefore, the locking means 22 of this embodiment are formed by the combination of the sub-part of an inner part of the radial element 20 and the sub-part of a outer part of the radial element 20 which are moveable relative to each other.

Some areas of the cylinder of the outer part of the locking means 22 are configured to act as stopping parts. Such areas are of resilient characteristics and can be flexed outside in radial direction. The two situations, namely flexed and unflexed are depicted in the two FIGS. 5a (flexed) and 5b (unflexed). The flexing of the stopper parts 24 is carried out by a relative movement between the inner part and the outer part of the locking means 22 against each other in the longitudinal direction of the actuator 10. Such movement in longitudinal direction is triggered by the length variation means 42 which pulls the inner part of the locking means 22 in the left direction. Following the pull of the length variation means 42, the inner part of the locking means 22 follows and slides along the corresponding ramps 26. Resulting from that relative movement, the stopper part 24 of the locking means 22 is flexed radial outward and thus is pressed against the outer wall of the cartridge 100. Due to that pressure, friction is build up between the stopper part 24 and the outer wall of the cartridge 100. Such friction prevents movement of the first radial element 20 in the longitudinal direction of the cartridge 100.

If the length variation means 42 is carrying out the extension movement, the aforesaid relative movement of the two parts of the locking means 22 is reversed and thus the locking means 22 are changed into unlocked position (see FIG. 5b).

It can be summarized that FIG. 5a shows the locking means 22 in locked and FIG. 5b in unlocked position. Both positions are independently from any outside control and are only triggered by the direction of the movement of the length variation means 42, in particular if they are on extension or contraction movement.

FIGS. 6a and 6b depict an embodiment of a second radial element 30 comprising second locking means 32. The second locking means 32 of this embodiment comprise in general two different parts. The inner part of the locking means 32 is of general circle profile and is coaxial with the longitudinal axis of the actuator 10 as well as of the cartridge 100. Outside of the inner part, an outer part is formed like a housing. Such housing is formed like an empty cylinder, closed on one end by a circle shaped plate. The other side of the cylinder is open to receive the inner part of the locking means 32. Both two parts touch each other through corresponding ramps 36.

Some areas of the cylinder of the outer part of the locking means 32 are configured to act as stopping parts 34. Such areas are of resilient characteristics and can be flexed outside in radial direction. The two situations, namely flexed and un-flexed are depicted in the two FIGS. 6a (un-flexed) and 6b (flexed). The flexing of the stopper parts 34 is carried out by a relative movement between the inner part and the outer part of the locking means 32 against each other in the longitudinal direction of the actuator 10. Such movement in longitudinal direction is triggered by extension of the length variation means 42 which pushes the inner part of the locking means 32 in the left direction (see FIG. 6b). Following such push of the length variation means 42 the inner part of the locking means 32 follows and slides along the corresponding ramps 36. Resulting from that relative movement, the stopper part 34 of the locking means 32 is flexed radial outward and thus is pressed against the outer wall of the cartridge 100. Due to that pressure, friction is build up between the stopper part 34 and the outer wall of the cartridge 100. Such friction prevents movement of the second radial element 30 in the longitudinal direction of the cartridge 100.

If the length variation means 42 is carrying out the contraction movement, the aforesaid relative movement of the two parts of the second locking means 32 is reversed and thus the locking means 32 are changed into unlocked position (see FIG. 6a).

The functionality of the second radial element 30 is comparable to the functionality of the first radial element 20 in the sense that both radial elements can be in a locked and in an unlocked position, depending on contraction or extension of the length variation means 42. However, when the length variation means 42 is in contracting movement the first radial element 20 is in locked position and the second radial element 30 is in unlocked position. Further, when the length variation means 42 is in extending movement the first radial element 20 is in unlocked position and the second radial element 30 is in locked position.

These opposite positions of radial elements 20, 30 are enabled by mechanical connection between the length variation means 40 and the locking means 22, 32. As described before, the locking means 22, 32 comprise corresponding ramps 26, 36, whereby the ramps are preferably arranged with the same direction of the gradient. I.e. the direction of the gradient of corresponding ramp 26 for the first locking means 22 in the first radial element 20 is the same as the direction of the gradient of the second corresponding ramp 36 for the second locking means 32 in the second radial element 30.

The length variation means 42 determines the length of the connecting element 40. Thus, during contraction of the connecting element 40 first radial element 20 is in locked position and second radial element 30 is in unlocked position. Furthermore, during extension of the connecting element 40 (the connecting element is extending) the first radial element 20 is in unlocked position and the second radial element 30 is in locked position. In other words, the first locking means 22 is in a locked position when the connecting element 40 is in a contracting length variation movement and the second locking means 32 is in a locked position when the connecting element 40 is in an extending length variation movement. Hence the actuator 10 moves in one direction upon movement of the length variation means 42. In conclusion the mechanical connection between the locking means 22, 32 and the length variation means 42 enables longitudinal movement of the actuator 10 in one direction by movement of the length variation means 42.

Both locking means 22 and 32 are only triggered by the movement direction of the length variation means 42 and not by any external control. In other words, the locking means 22 and 32 are passive locking means. They do not comprise actuators or active drive means, such as shape memory alloy, piezo-electric elements, paraffin, or the like. They merely act upon their mechanical construction.

The functionality and the dependencies between the length variation means 42 and the two locking means 22 and 32 is also shown in the diagrams of FIG. 7. It can be seen in such diagrams that the locking an unlocking of both locking means 22 and 32 follows the movement of the length variation means 42 in extended direction or contracted direction. Both locking means 22 and 32 act, for example by the orientation of ramps 26 and 36, contrary. In other words, when one locking means 22 is locked the other one 32 is unlocked and the other way round.

Figure 8:
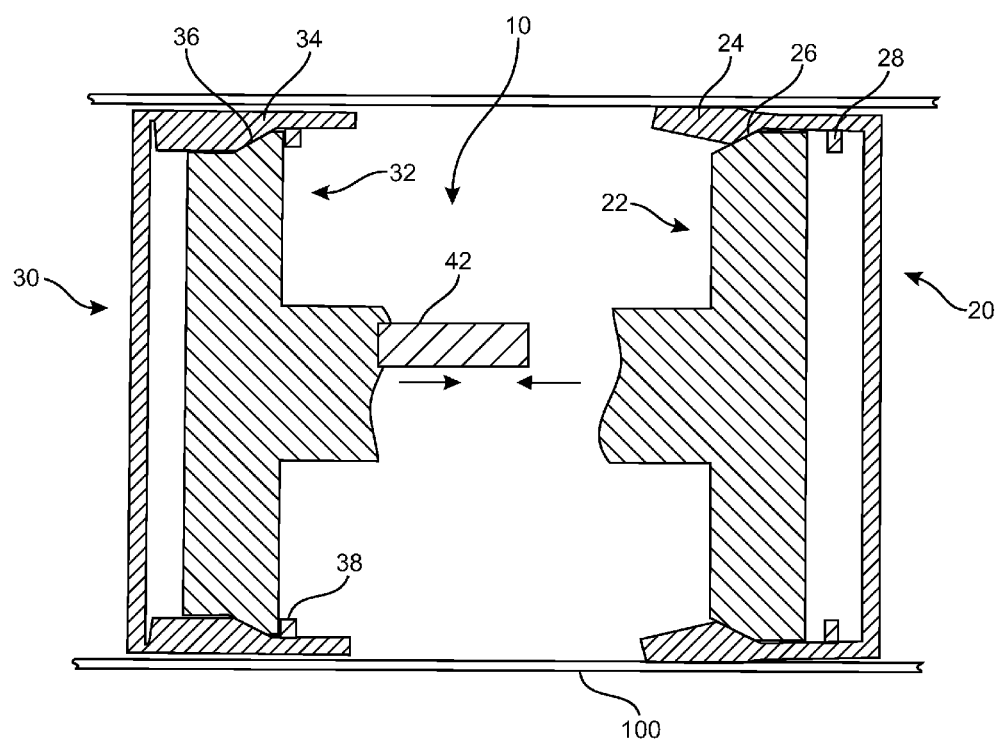
FIG. 8 illustrates a further embodiment of an inventive actuator with the locking means of the first radial element in locking position
Figure 9:
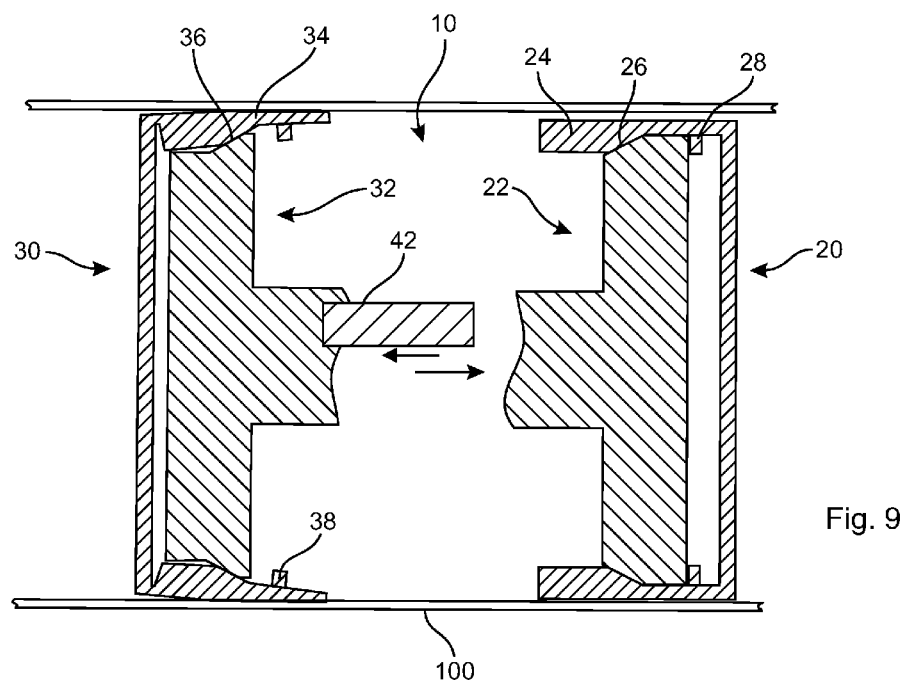
FIG. 9 illustrates an embodiment of FIG. 8. with the locking means of the second radial means in locking position

FIGS. 8 and 9 show a further embodiment of an inventive actuator 10. The locking means 22 and 32 are similar to the embodiments of FIGS. 5a, 5b, 6a and 6b, but additionally blocks 28 and 38 are provided. Such blocks are located in the direction away from the ramps 26 and 36 and may be used to support directing the extension or contraction of the length variation means 42 towards one radial element or the other radial element, respectively. Therefore, if one of the locking means 22 or 32 is in unlocked position, the length variation means 42 can carry out its movement in extension or contraction direction and therefore push or pull, respectively, the first or the second radial element 20 or 30, respectively. FIG. 8 depicts the situation during the contraction movement of the length variation means 42 and FIG. 9 shows the situation during the extension or contraction movement of the length variation means 42.

Exemplary embodiments of the present invention have been described. Those skilled in the art will understand, however, that changes and modifications may be made to these embodiments without departing from the true scope and spirit of the present invention, which is defined by the claims.

The invention claimed is:

1. An actuator for dispensing fluid from a cartridge, the actuator being configured to be moveable within the cartridge along the longitudinal axis of the cartridge and comprising:
   a first radial element configured to face the dispensing opening of the cartridge,
   a second radial element configured to face in the opposite direction than the first radial element and
   a connecting element connecting the first and the second radial element and configured to have a length along the longitudinal axis of the cartridge,
   wherein the connecting element comprises a length variation element configured to change the longitudinal length of the connecting element,
   wherein the first radial element comprises a first lock and the second radial element comprises a second lock, and
   wherein the locks are configured for releasably locking each of the first and the second radial element separately against movement along the longitudinal axis of the cartridge and to be activated and released by the length variation element depending on the change of the longitudinal length of the connecting element,
   wherein the locks comprise stopping parts which are configured to move in the radial direction of the actuator to engage the cartridge when one of the first or second radial elements is in a locked position,
   wherein the locks are passive locks, without active drive, triggered by the change of the longitudinal length of the connecting element.

2. The actuator according to claim 1, wherein the first lock is in a locked position when the length variation element of the connecting element is in a contracting length variation movement and the second lock is in a locked position when the length variation elements of the connecting element is in a extending length variation movement.

3. The actuator according to claim 1, wherein the lock is configured to releasably engage with the outer wall of the cartridge, wherein the engagement will lock the lock and prevent the lock from movement along the longitudinal axis of the container or cartridge.

4. The actuator according to claim 1, wherein the lock is configured to support longitudinal movement of the actuator in one direction by the length variation movement of the length variation element.

5. The actuator according to claim 1, wherein the first lock and the second lock comprise a mechanical connection to the length variation means for activation and release of the lock.

6. The actuator according to claim 1, wherein when the length variation element is moved from the extended position to the contracted position, the second lock of the second radial element is caused to unlock and the first lock of the first radial element is caused to lock.

7. The actuator according to claim 1, wherein each lock comprises at least two parts being moveable against each other in longitudinal direction of the actuator.

8. The actuator according to claim 1, wherein the lock comprises corresponding ramps to coordinate activation and release of the lock of the radial elements by length variation movement of the length variation element, whereby the corresponding ramps are arranged such that the direction of the gradient of corresponding ramp for the first lock in the first radial element is the same as the direction of the gradient of the second corresponding ramp for the second lock in the second radial element.

9. The actuator according to claim 8, wherein the first radial element further comprises an interface element configured to transfer the movement of the actuator to the fluid contained within the cartridge.

10. The actuator according to claim 9, wherein the interface element is releasably connected to the first radial element of the actuator.

11. The actuator according to claim 9, wherein the interface element comprises a circumferential seal for sealing the fluid against leaking between the first radial element and the cartridge.

12. The actuator according to claim 9, wherein the interface element comprises a geometry for transferring the movement of the actuator to passive closing element positioned in the cartridge.

13. The actuator according to claim 1, wherein the length variation element reacts upon internal stimulation from inside the actuator and comprises at least one of a shape memory metal, a piezoelectric part, a static magnet, and a dynamic magnet.

14. The actuator according to claim 1, wherein the length variation element reacts upon external stimulation from outside of the actuator and comprises at least one of a shape memory metal, a piezoelectric part, a static magnet, and a dynamic magnet.

15. The actuator according to claim 1, wherein that the actuator further comprises pull back element configured to move the actuator away from the dispensing opening of the cartridge.

16. A system comprising at least one cartridge, at least one actuator of claim 1, and at least one control element configured to vary at least the length variation element of the actuator.

17. A system comprising an actuator according to claim 15 and further comprising a second actuator for dispensing fluid from a second container.

18. A method for dispensing a fluid from a container utilizing an actuator according to claim 1, characterized in that the maximum length variation of the length variation element is smaller than the length variation necessary for one delivery step of delivering the fluid from the container.

19. A method for dispensing a fluid from a container utilizing an actuator according to claim 1, characterized in that the maximum variation of the length variation elements is greater or equal than the length variation necessary for one delivery step of delivering liquid from the container.

* * * * *